(12) United States Patent
Sachs et al.

(10) Patent No.: US 8,712,124 B2
(45) Date of Patent: Apr. 29, 2014

(54) ARTIFACT REMOVAL IN NUCLEAR IMAGES

(75) Inventors: Jonathan Sachs, Haifa (IL); Floribertus Philippus Martinus Heukensfeldt Jansen, Ballston Lake, NY (US); Lana Volokh, Haifa (IL); Yaron Hefetz, Herzeliya (IL)

(73) Assignee: General Electric Company, Schenectady, NY (US)

( * ) Notice: Subject to any disclaimer, the term of this patent is extended or adjusted under 35 U.S.C. 154(b) by 183 days.

(21) Appl. No.: 13/165,527

(22) Filed: Jun. 21, 2011

(65) Prior Publication Data

US 2012/0328173 A1    Dec. 27, 2012

(51) Int. Cl.
*G06T 5/00*    (2006.01)
*G06K 9/00*    (2006.01)

(52) U.S. Cl.
USPC .......................................... 382/128; 382/131

(58) Field of Classification Search
None
See application file for complete search history.

(56) References Cited

U.S. PATENT DOCUMENTS

| | | | |
|---|---|---|---|
| 5,504,334 A | 4/1996 | Jansen et al. |
| 5,689,116 A | 11/1997 | Jansen |
| 5,929,447 A | 7/1999 | Crandall et al. |
| 5,932,878 A | 8/1999 | Jansen et al. |
| 5,936,248 A | 8/1999 | Jansen |
| 6,051,837 A | 4/2000 | Jansen |
| 6,242,745 B1 | 6/2001 | Berlad et al. |
| 6,252,232 B1 | 6/2001 | McDaniel et al. |
| 6,356,619 B1 | 3/2002 | Nagy et al. |
| 6,388,258 B1 | 5/2002 | Berlad et al. |
| 6,574,301 B1 | 6/2003 | Jansen |
| 7,211,799 B2 | 5/2007 | Jansen et al. |
| 7,227,149 B2 | 6/2007 | Stearns et al. |
| 7,301,144 B2 | 11/2007 | Williams et al. |
| 7,312,455 B2 | 12/2007 | Manjeshwar et al. |
| 7,328,623 B2 | 2/2008 | Slagle et al. |
| 7,332,724 B2 | 2/2008 | Hefetz et al. |
| 7,339,174 B1 | 3/2008 | Hugg et al. |
| 7,345,281 B2 | 3/2008 | Jansen et al. |
| 7,375,338 B1 | 5/2008 | Hugg et al. |
| 7,381,959 B2 | 6/2008 | Manjeshwar et al. |
| 7,405,405 B2 | 7/2008 | Stearns et al. |
| 7,408,163 B2 | 8/2008 | Hefetz |
| 7,439,514 B1 | 10/2008 | Uribe et al. |
| 7,470,907 B2 | 12/2008 | Hugg et al. |

(Continued)

FOREIGN PATENT DOCUMENTS

WO    WO 2010032163 A1 *    3/2010

OTHER PUBLICATIONS

U.S. Appl. No. 13/165,562, filed Jun. 21, 2001, Jonathan Sachs et al.
U.S. Appl. No. 13/019,590, filed Feb. 2, 2011, Bouhnik.

*Primary Examiner* — Stephen R Koziol
*Assistant Examiner* — Amandeep Saini
(74) *Attorney, Agent, or Firm* — Fletcher Yoder, P.C.

(57) ABSTRACT

The present disclosure relates various approaches for removing or reducing the effects of out-of-field sources of radiation if emission tomography applications. In certain embodiments, a plurality of measured views are acquired about an organ or region of interest. The measured views may be reconstructed to form an image and the image may be used in a cleaning or correction process that allows generation of a final image having reduced or eliminated artifacts attributable to out-of-field source effects.

19 Claims, 7 Drawing Sheets

(56) References Cited

U.S. PATENT DOCUMENTS

| | | |
|---|---|---|
| 7,495,225 B2 | 2/2009 | Hefetz et al. |
| 7,514,885 B2 | 4/2009 | Hausner et al. |
| 7,518,114 B2 | 4/2009 | Ganin et al. |
| 7,531,807 B2 | 5/2009 | Hefetz |
| 7,557,352 B2 | 7/2009 | Hefetz |
| 7,569,826 B2 | 8/2009 | Uribe et al. |
| 7,592,596 B2 | 9/2009 | Klein et al. |
| 7,592,597 B2 | 9/2009 | Hefetz et al. |
| 7,671,331 B2 | 3/2010 | Hefetz |
| 7,671,340 B2 | 3/2010 | Uribe et al. |
| 7,676,869 B2 | 3/2010 | Zelnik et al. |
| 7,680,240 B2 * | 3/2010 | Manjeshwar et al. ............ 378/4 |
| 7,692,160 B2 | 4/2010 | Lee et al. |
| 7,693,565 B2 | 4/2010 | Shai et al. |
| 7,723,688 B2 | 5/2010 | Hefetz |
| 7,723,690 B2 | 5/2010 | Uribe et al. |
| 7,829,856 B2 | 11/2010 | Jansen et al. |
| 7,902,511 B2 | 3/2011 | Thielemans et al. |
| 8,010,184 B2 | 8/2011 | Avila et al. |
| 8,022,357 B2 | 9/2011 | Amir et al. |
| 8,067,744 B2 | 11/2011 | Blevis et al. |
| 8,103,329 B2 | 1/2012 | Fomitchov et al. |
| 8,126,537 B2 | 2/2012 | Yakubovsky et al. |
| 2004/0227091 A1 | 11/2004 | LeBlanc et al. |
| 2007/0092447 A1 | 4/2007 | Padilla de Jesus et al. |
| 2008/0004533 A1 | 1/2008 | Jansen et al. |
| 2008/0304619 A1 | 12/2008 | Blevis et al. |
| 2010/0220909 A1 | 9/2010 | Thielemans et al. |
| 2011/0297838 A1 | 12/2011 | Wangerin et al. |
| 2012/0051664 A1 | 3/2012 | Gopalakrishnan et al. |

* cited by examiner

ARTIFACT REMOVAL IN NUCLEAR IMAGES

BACKGROUND OF THE INVENTION

The subject matter disclosed herein relates to nuclear imaging, and more particularly to correction of artifacts caused by out-of-field source in nuclear imaging techniques, such as single photon emission computed tomography (SPECT) or other emission based tomography approaches.

A variety of imaging techniques are known and currently in use, such as for medical diagnostic applications. Certain such techniques, such as SPECT, rely on the emission of gamma rays during the radioactive decay of a radioisotope (or radionuclide), commonly administered in the form of a radiopharmaceutical agent that can be carried by, and in some cases, bound to particular tissues of interest. Such nuclear imaging technologies detect the emissions via a suitable gamma radiation detector. In particular, a suitable gamma radiation detector may consist of components which, in response to incident radiation, generate image data related to the quantity of radiation impacting the individual regions of the detector. The image data generated by the detector components may then be reconstructed to generate images of internal structures of the subject.

While such systems have proven extremely useful at providing high quality images with good diagnostic value, further refinement is possible. For example, in some instances, a particular portion of a patient's anatomy may be of interest to a clinician. In such instances, the clinician may attempt to obtain image data related to the organ of interest. However, due to the manner in which data is collected, typically from a large number of views or angles about the patient, certain of the collected data may include data that represents not only the region of interest to the clinician, but other portions of the patient anatomy that may not be of interest. For example, other organs or regions of the patient may participate in the breakdown of the radiopharmaceutical agent and may thus emit gamma rays beyond the background level otherwise observed. To the extent that these other organs or regions are visible in the image data collected at certain views, the quality of the images generated for the actual region of interest may be impacted. This effect may be present in small field of view cameras where the size of the imaging detectors is limited and with cameras where the detectors are specifically aimed at the organ of interest. Similarly, the difficulty may be present in PET (Positron Emission Tomography) when using a detector which is not a full circle.

BRIEF DESCRIPTION OF THE INVENTION

The present disclosure relates to approaches by which aspects of an acquired nuclear imaging data set (such as a SPECT data set or other emission based imaging modality) that relate to contributions from portions of patient anatomy other than a region of interest (i.e., out-of-field sources) are reduced or eliminated. In certain implementations, a reconstruction approach, such as an iterative reconstruction approach, may be employed in which modeled or expected image data may be used to reduce or eliminate data contributions from unexpected or unwanted sources. In this manner, images may be generated that correspond to the data acquired from a region of interest of the patient (such as the heart) while reducing or excluding the effects of data that is associated with other regions that may be inadvertently imaged during the data acquisition process.

In accordance with one aspect of the present disclosure, an image analysis system is provided. The image analysis system includes one or more processing components configured to receive measured views that generally encompass an organ or region of interest. At least some of the measured views include radiation contributions from outside the organ or region of interest, and to execute one or more executable routines stored in a memory. The one or more processing components are also configured to execute one or more executable routines stored in a memory. The stored routines, when executed, reconstruct the measured views to generate an initial image, generate a corresponding estimated view for each measured view using the initial image, compare each measured view with the corresponding estimated view to derive an indication, if any, of the radiation contributions from outside the organ or region of interest present in each measured view, and use the indications to reconstruct a final image in which the radiation contributions from outside the organ or region of interest are reduced or eliminated. The image analysis system also includes interface circuitry configured to allow user interaction with the image analysis system.

In accordance with another aspect, one or more machine readable media are provided that encode routines. The routines when executed by a processor, cause acts to be performed that include: accessing a plurality of different measured views. The measured views depict a radiation contribution from an organ or region of interest. One or more of the measured views also include a secondary radiation contribution from outside the organ or region of interest. The performed acts also include reconstructing an initial image using the plurality of measured views, segmenting the organ or region of interest in the initial image to form a mask, and re-projecting the initial image using the mask to generate a plurality of cleaned views in which those pixels outside the area defined by the mask are set to an adjusted value. A final image is reconstructed based at least in part upon the plurality of cleaned views.

In accordance with a further aspect, an image reconstruction method is provided. In accordance with this method, a plurality of measured views are acquired that generally represent the radiation emitted by an organ or region of interest as seen from different positions. One or more of the measured views includes radiation emitted by an out-of-field source with respect to the fields-of-view of at least some of the remaining measured views. A corresponding estimated view is generated for each measured view. Each measured view and corresponding estimated view are compared to identify one or more affected regions in the one or more measured views that include radiation emitted by the out-of-field source. A final image is generated where the contributions of the identified affected regions are reduced or eliminated.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

As discussed herein, the present disclosure relates to the generation of nuclear medicine images, such as SPECT or other emission based tomographic reconstructions, in which the effects of out-of-field sources are reduced or removed. For example, in one embodiment, a reconstruction approach, such as an iterative reconstruction approach, may be employed in which expected or modeled views related to the actual organ or physiology of interest are compared to the actual measured views for those portions of the measured image data that are attributable to in-field sources. The portions of the image data that are affected by the out-of-field sources may be rejected, replaced, corrected, weighted downward, and so forth as part of the reconstruction process. In this manner, images of the region of interest of the patient may be reconstructed such that the effects of such out-of-field sources are reduced or eliminated. This effect may be present in small field of view cameras where the size of the imaging detectors is limited and with cameras in which the detectors are specifically aimed at the organ of interest. The problem was seldom encountered in large field of view SPECT cameras in which the entire section of the imaged body is within each and every view (sometimes called projection). However, using small field of view detectors may be a necessity, or may bring a better cost effectiveness, and detectors specifically aimed at the organ of interest may yield better sensitivity, improved resolution, reduced dose to the patient, improved throughput and/or greater patient comfort due to reduced acquisition time.

Figure 1:
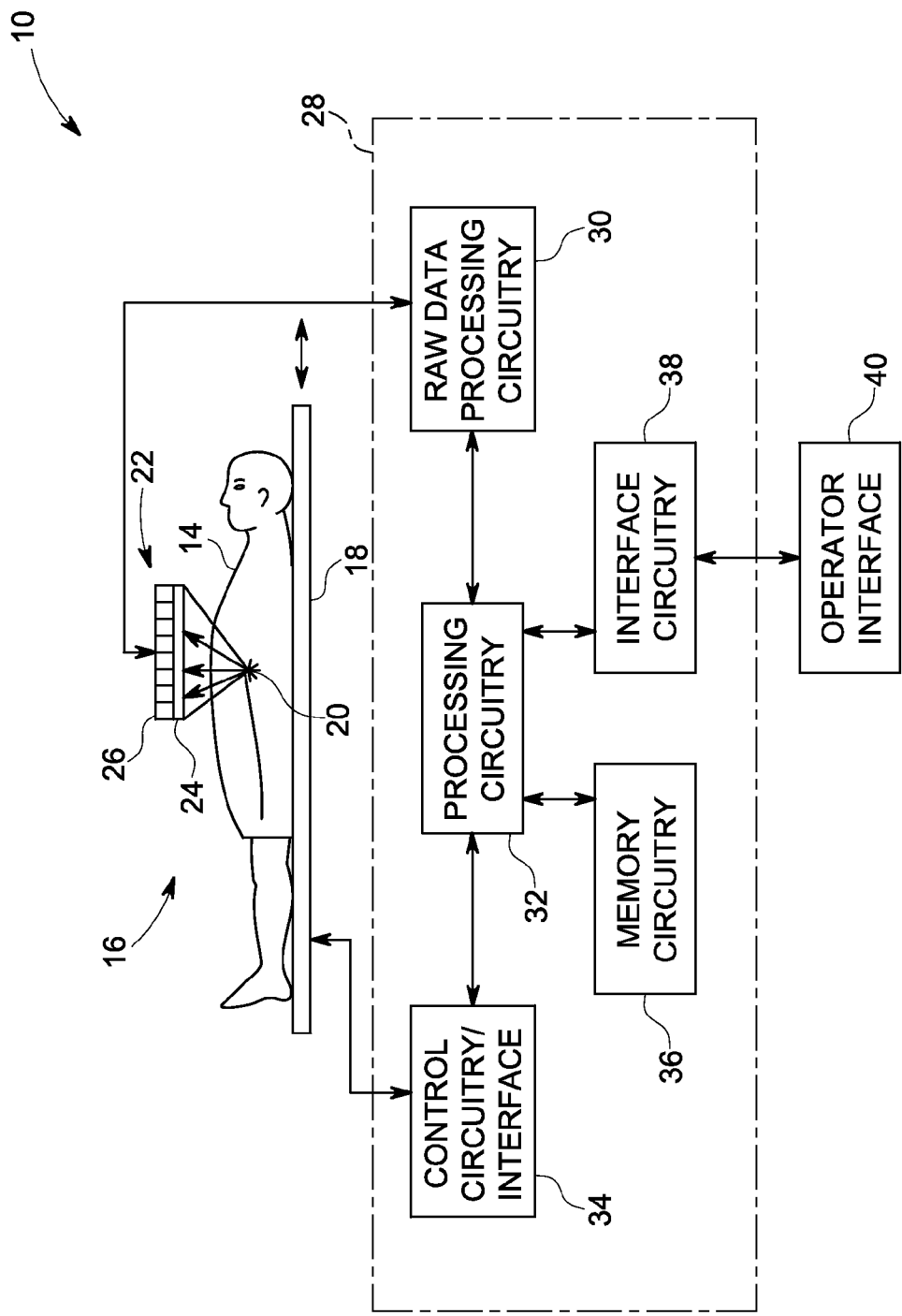
FIG. 1 is a diagrammatical representation of an embodiment of a SPECT imaging system suitable for use in accordance with the present disclosure.

With the foregoing discussion in mind, a diagrammatic representation of one example of a SPECT imaging system suitable for use with the present approach is shown in FIG. 1. As will be appreciated, the approaches discussed herein may also be suitable for use with other emission based tomographic modalities. The system of FIG. 1, designated generally by the reference numeral 10, is designed to produce useful images of a subject 14 using suitable detector components (such as pin-hole gamma cameras or collimated gamma cameras having solid state or scintillating detectors) as described in detail below. The subject is positioned in a scanner, designated by reference numeral 16, in which a patient support 18 is positioned. The support may be movable within the scanner to allow for imaging of different tissues or anatomies of interest 20 within the subject. Prior to image data collection, a radioisotope, such as a radiopharmaceutical substance (sometimes referred to as a radiotracer), is administered to the patient, and may be bound or taken up by particular tissues or organs 20. Typical radioisotopes include various radioactive forms of elements, although many in SPECT imaging are based upon an isotope of technetium ($^{99m}$Tc) that emits gamma radiation during decay. Various additional substances may be selectively combined with such radioisotopes to target specific areas or tissues 20 of the body.

Gamma radiation emitted by the radioisotope is detected by a detector component 22, such as a digital detector or gamma cameras. Although illustrated in the figure as a planar device positioned above the patient to simplify illustration, in practice the detector structure(s) 22 may be positioned about the patient, such as in an arc or ring about the patient, or may be attached to a positioner (e.g., a C-arm, gantry, or other movable arm) that allows the detector structure(s) 22 to be moved in an arc or orbit about the patient during data acquisition, or to change orientation in respect to the patient during data acquisition. In general, the detector structure(s) 22 typically include one or more components or elements capable of sensing gamma radiation or otherwise generating a detectable signal in response to such radiation. In the illustrated embodiment, the detector structures comprise one or more collimators and a scintillator, together represented generally as reference numeral 24. The collimator allows gamma radiation emitted only in certain directions (typically perpendicular to the scintillator) to impact the scintillator. The scintillator, which is typically made of a crystalline material, such as sodium iodide (NaI), converts the received gamma radiation to lower energy light energy (e.g., in an ultraviolet range). Photomultiplier tubes 26 then receive this light and generate image data corresponding to photons impacting specific discrete picture element (pixel) regions. In other embodiments, the detector structure 22 may not be collimated but may instead use other gamma radiation sensing technologies, such as one or more pinhole gamma cameras, as also discussed herein.

In the depicted embodiment, the detector structure(s) 22 is coupled to system control and processing circuitry 28. This circuitry may include a number of physical and/or software components that cooperate to allow the collection and processing of image data to create the desired images. For example, the circuitry may include raw data processing circuitry 30 that initially receives the data from the detector structure(s) 22, and that may perform various filtering, value adjustments, and so forth. Processing circuitry 32 allows for the overall control of the imaging system, and for manipulation and/or reconstruction of image data. The processing circuitry 32 may also perform calibration functions, correction functions, and so forth on the data. The processing circuitry 32 may also perform image reconstruction functions, such as based on known algorithms (e.g., back projection, iterative reconstruction, and so forth). Such functions may also be performed in post-processing on local or remote equipment. As will be appreciated, the various image reconstruction and artifact correction algorithms discussed herein may be implemented in part or in their entirety using one or both of the raw data processing circuitry 30 and/or the processing circuitry 32.

In the depicted embodiment, the processing circuitry 32 interacts with control circuitry/interface 34 that allows for control of the scanner and its components, including the patient support, camera, and so forth. Moreover, the processing circuitry 32 will be supported by various circuits, such as memory circuitry 36 that may be used to store image data, calibration or correction values, routines performed by the processing circuitry (such as the artifact correction algorithms disclosed herein), and so forth. In one embodiment, the processing circuitry executes one or more iterative reconstruction algorithms that may utilize approaches for reducing or removing out-of field source effects as discussed herein. Such iterative reconstruction approaches may generally utilize iterated comparisons between expected or model images and observed or measured image data to reduce artifacts or irregularities attributable to non-physiological factors, such as factors related to imaging system geometry, out-of-source field effects, attenuation, scatter and so forth. In such an iterative reconstruction approach, the convergence process or loop may be repeated or iterated for a specified number of iterations, or until some completion criteria is met, such as minimization of a cost function.

Finally, the processing circuitry may interact with interface circuitry 38 designed to support an operator interface 40. The operator interface allows for imaging sequences to be commanded, scanner and system settings to be viewed and adjusted, images to be viewed, and so forth. In the illustrated embodiment, the operator interface includes a monitor 42 on which reconstructed images 12 may be viewed.

In an institutional setting, the imaging system 10 may be coupled to one or more networks to allow for the transfer of system data to and from the imaging system, as well as to permit transmission and storage of image data and processed images. For example, local area networks, wide area networks, wireless networks, and so forth may allow for storage of image data on radiology department information systems and/or on hospital information systems. Such network connections further allow for transmission of image data to remote post-processing systems, physician offices, and so forth.

In one implementation, a nuclear imaging system, such as the SPECT imaging system of FIG. 1, may be configured to image targeted or limited regions of the body of the patient, such as specific organs of interest. For example, some such systems may be configured for cardiac imaging and may include multi-pinhole or dedicated cardiac cameras having small or limited fields of view. In such implementations, the volume of reconstruction is typically smaller than the portion of the patient in view of the camera and may be only slightly larger than the organ or region of interest (e.g., the heart or other organ).

In typical implementations, image data may be acquired for a variety of different views with respect to the patient. As a result of these differing views, certain of the views may detect emitted gamma rays that are outside of the field of view associated with other views and that are outside of the region corresponding to the volume to be reconstructed (i.e., the volume of reconstruction). When such image data from out-of-field sources is present, the image reconstruction process is mathematically inconsistent as data from the out-of-field sources cannot be reconstructed into the volume of reconstruction. These mathematical inconsistencies may manifest themselves as artifacts in the reconstructed image volume.

By way of example, in a cardiac camera implementation, the liver may be seen in the data corresponding to one or more of the angular views but not in other views. For example, turning to FIGS. 2-6, a configuration of multiple pinhole cameras 60 is depicted in which pinhole cameras 60 are placed at or moved between various view angles (labeled A-D) about a patient 14. Each pinhole camera 60 has an associated field of view 62 from a given view angle, as depicted by respective dashed lines, that corresponds to the portion of the patient 14 for which image data is acquired by the pinhole camera 60 at that view. As will be appreciated, pinhole cameras 60 such as those depicted generally acquire conical projections corresponding to an inverted image of the field-of-view 62 from the respective camera 60.

Figure 2:
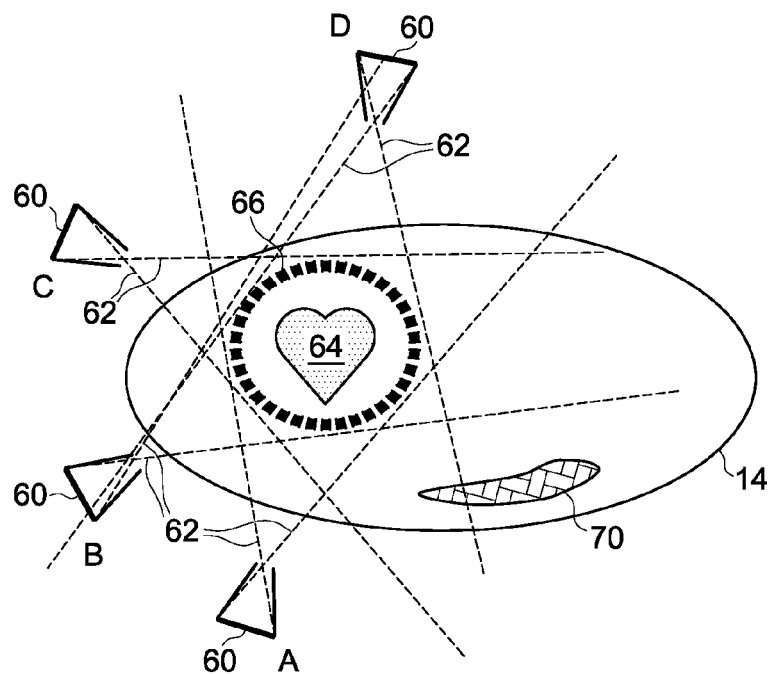
FIG. 2 depicts an example of a SPECT image acquisition occurring over a variety of views using pinhole camera type gamma detectors, in accordance with aspects of the present disclosure.

In the depicted example, a cardiac imaging implementation is depicted such that the fields of view 62 encompass the heart 64 of the patient 14, i.e., the heart 64 constitutes the region or organ of interest. The combined fields of view 62 define a volume of reconstruction 66 corresponding to a region for which image data is acquired from each view and which generally encompasses the region or organ of interest, here heart 64. It should be noted that for drawing clarity, FIG. 2 shows four pinhole gamma cameras in a plane. The actual camera system geometry may have more such cameras arranged in a three-dimensional arrangement, e.g., the views need not all be in the same plane.

Outside of the volume of reconstruction 66 may be one or more other organs or structures which may also serve as locations from which gamma rays may be emitted, such as due to the clearing or circulatory functions performed by those organs. In the depicted example, one such organ is the liver 70, which is visible in some, but not all, of the fields of view 62 of the respective multi-pinhole cameras 60. By way of example, and turning now to FIGS. 3-6, various images 72, 74, 76, 78 corresponding to the image data acquired by the respective pinhole gamma camera 60 at respective views A-D are depicted.

Figure 3:
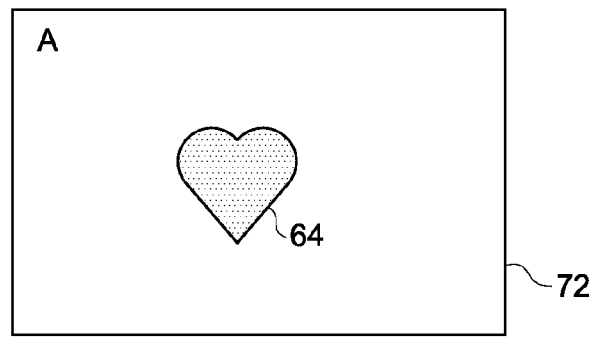
FIG. 3 depicts an image acquired at a first view by the image acquisition configuration depicted in FIG. 2.

For example, turning to FIG. 3, a stylized example of a cardiac image 72 acquired by the SPECT system configuration of FIG. 2 is depicted. In this example, the image 72 depicted in FIG. 3 is acquired by a pinhole camera 60 at view position A of FIG. 2. From view position A, the field-of-view 62 of the respective pinhole camera 60 encompasses the region or organ of interest, here the heart 64, without contribution from other sources.

Figure 4:
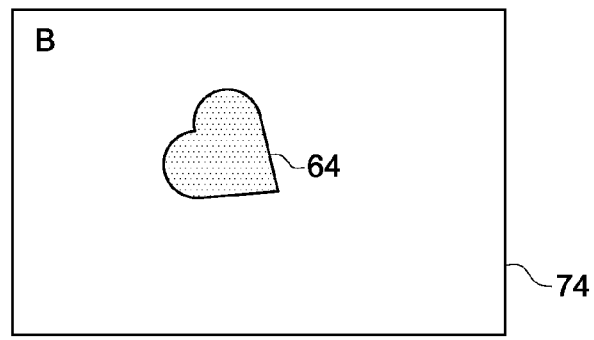
FIG. 4 depicts an image acquired at a second view by the image acquisition configuration depicted in FIG. 2.

Turning to FIG. 4, a stylized example of another cardiac image 74 is depicted which corresponds to an image acquired by the SPECT system configuration of FIG. 2 at view position B. As with the respective image 72 acquired at view position A, the field-of-view 62 of the respective pinhole camera 60 at view position B encompasses the region or organ of interest, e.g., heart 64 (seen from a different perspective), without contribution from other sources. The image 72 acquired at view A and the image 74 acquired at view B, however, differ in that the region of interest, e.g., heart 64, is imaged from different views, thus, depicting the region of interest from different respective view angles.

Figure 5:
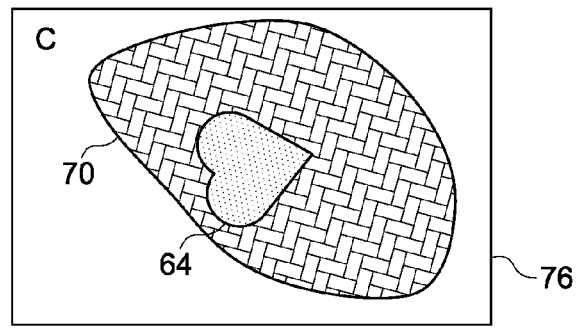
FIG. 5 depicts an image acquired at a third view by the image acquisition configuration depicted in FIG. 2.

In FIG. 5, a stylized example of another cardiac image 76 is depicted which corresponds to an image acquired by the SPECT system configuration of FIG. 2 at view position C. Unlike images 72 and 74 acquired at respective view position A and B, the field-of-view 62 of the respective pinhole camera 60 at view position C encompasses not only the region or organ of interest, e.g., heart 64, but also a source of gamma rays outside the region of interest, in this example the liver 70, i.e., an out-of-field source of gamma rays. Indeed, in the depicted example, the heart 64 and liver 70 overlap from the viewing perspective of the pinhole camera 60 at view position C. Thus, image data 76 acquired by the pinhole camera 60 at view C, includes contributions from out-of-field sources (e.g., liver 70) that may result in artifacts when reconstructing the volume of interest encompassing the heart 64.

Figure 6:
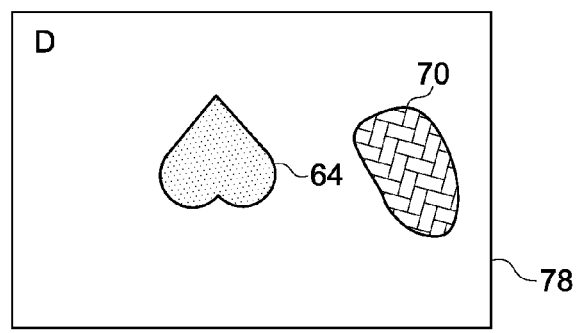
FIG. 6 depicts an image acquired at a fourth view by the image acquisition configuration depicted in FIG. 2.

Likewise, FIG. 6 depicts a final stylized example of a cardiac image 78 corresponding to an image acquired by the SPECT system configuration of FIG. 2 at view position D. As with image 76, the field-of-view 62 of the respective pinhole camera 60 at view position D encompasses both the region of interest (e.g., heart 64) as well as an out-of-field source (e.g., liver 70). However, unlike image 76, in cardiac image 78 the heart 64 and liver 70 do not overlap within the field-of-view, though the gamma ray data associated with the liver 70 may still contribute to artifacts within the volume of reconstruction 66 that includes the region of interest (e.g., heart 64). However, even though the liver 70 and heart 64 do not overlap in this example, radiation from the liver may still affect reconstruction of images of the heart in this view, such as due to radiation scatter effects.

Figure 7:
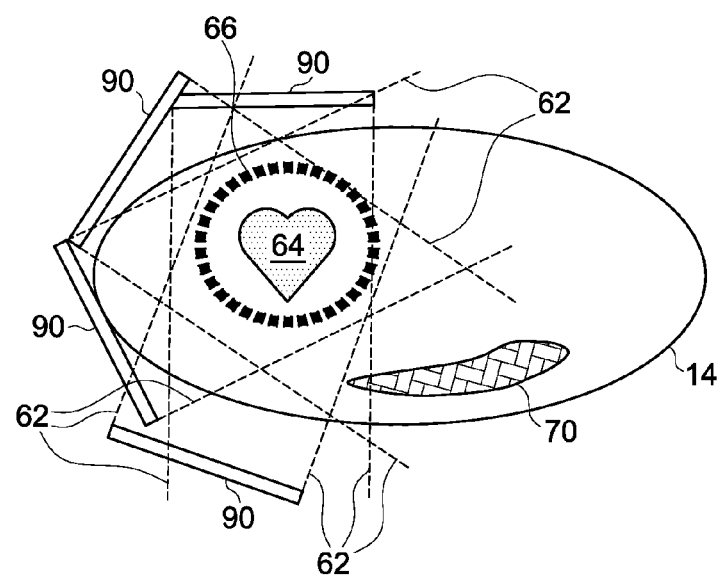
FIG. 7 depicts an example of a SPECT image acquisition occurring over a variety of views using collimated gamma detector assembly, in accordance with aspects of the present disclosure.

The preceding example describes one example of an image acquisition configuration employing pinhole cameras 60 which, as noted above, generally acquire conical projections corresponding to an inverted image of the field-of-view 62 from the camera 60. In other embodiments, a collimated detector assembly 90 or collimated camera may be employed, as depicted in FIG. 7, which employs both a collimator and panel detector within the assembly. The collimator in such an assembly 90 acts to limit the angular range of gamma rays striking the detector panel, thereby helping to localize the gamma ray emission. In such an image acquisition configuration, the collimated detector assembly 90 has a limited, non-inverted field-of-view 62 that does not expand with distance, unlike the pinhole camera configuration. As with the pinhole camera image acquisition discussed with respect to FIGS. 2-6, images acquired at various views A-D using the depicted collimated detector assembly may include image data from outside the volume of reconstruction 66, such as from liver 70.

Figure 8:
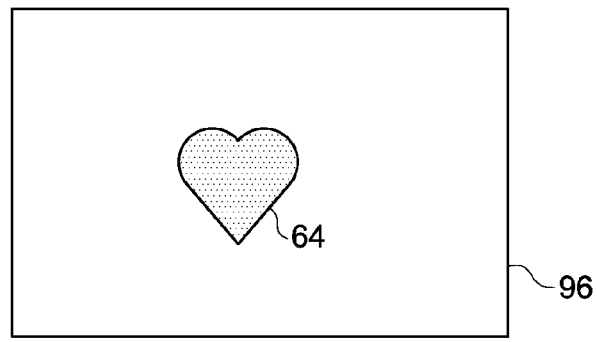
FIG. 8 depicts an image acquired at a first view by the image acquisition configuration depicted in FIG. 7.
Figure 9:
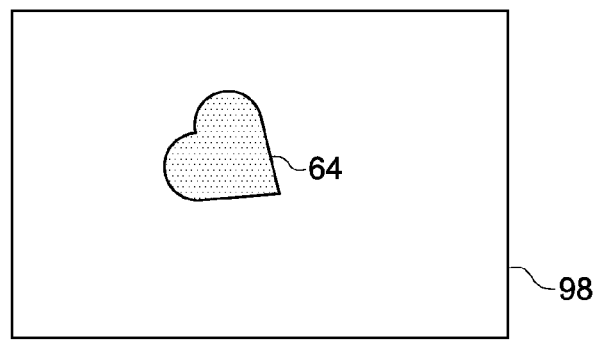
FIG. 9 depicts an image acquired at a second view by the image acquisition configuration depicted in FIG. 7.

Turning to FIG. 8, a stylized example of a cardiac image 96 acquired by the SPECT system configuration of FIG. 7 is depicted. In this example, the image 96 is acquired using a collimated detector assembly 90 at view position A of FIG. 7. From view position A, the field-of-view 62 of the collimated detector assembly 90 encompasses the region or organ of interest, here the heart 64, without contribution from other sources. Likewise, cardiac image 98 of FIG. 9 depicts a representative, stylized image as may be acquired by a collimated detector assembly 90 at view position B of FIG. 7, and which, therefore, depicts the region of interest, e.g., heart 64, from a different view angle.

Figure 10:
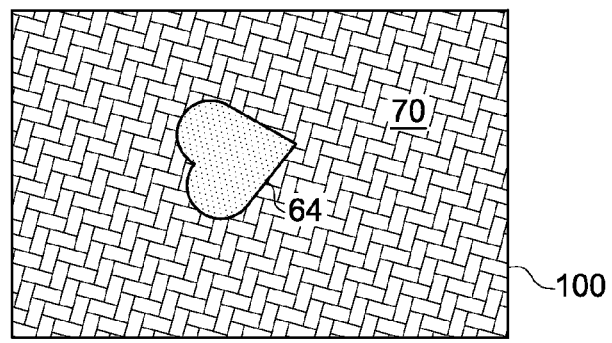
FIG. 10 depicts an image acquired at a third view by the image acquisition configuration depicted in FIG. 7.
Figure 11:
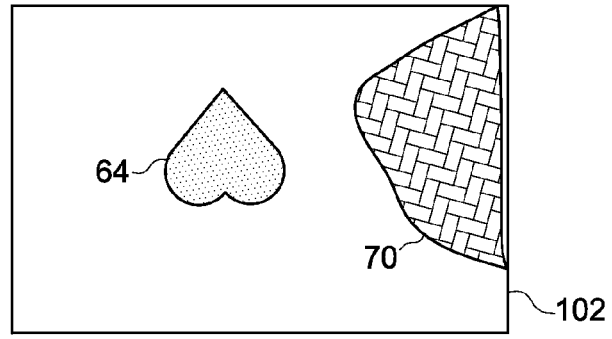
FIG. 11 depicts an image acquired at a fourth view by the image acquisition configuration depicted in FIG. 7.

Likewise, FIGS. 10 and 11 respectively depict images 100 and 102 that may be acquired using the collimated detector assembly 90 of FIG. 7 at respective view positions C and D. As depicted in image 100 and 102, an out-of-field source of gamma emission, here represented by liver 70 may be present in the field of view 62 associated with certain view positions. As a result, the out-of-field source may contribute to the image data acquired at those view positions, either separately from the region or organ of interest, e.g., heart 64 (image 102, FIG. 11), or overlapping with the region or organ of interest (image 100, FIG. 10). As noted in the previous example, volumes reconstructed using image data that includes contributions from such out-of-field sources may include artifacts or other irregularities.

With the foregoing in mind, it will be noted that the data measured by the depicted SPECT imaging systems consist of a set of measured views that are generally dominated by radiation emitted by the organ or region of interest. This set of measured views constitutes data that may in turn be reconstructed to generate a volume of interest that includes the region or organ of interest.

To the extent that radiation from out-of-field sources may be present, such radiation typically contributes to a limited number of the measured views, and thus is not constant or uniform between measured views. When present, such out-of-field source radiation may appear as contiguous or uniform regions, though in some instances the out-of-field source radiation may be patterned depending on the organs at issue, system geometry and so forth. Further, such out-of-field source radiation may or may not overlap the organ or region of interest, depending on the measured view in question.

Out-of-field source radiation, when present, may result in a count density that is larger than the observed background radiation and that is comparable to or larger than the count density associated with the organ or region of interest in the affected measured views. As a result, it may be desirable to identify the measured count data associated with an out-of-field source from the measured count data associated with the organ or region of interest. Such identification of the data associated with an out-of-field source may allow this data to be separated from the affected measured views while leaving the signal associated with the organ or region of interest intact.

Figure 12:
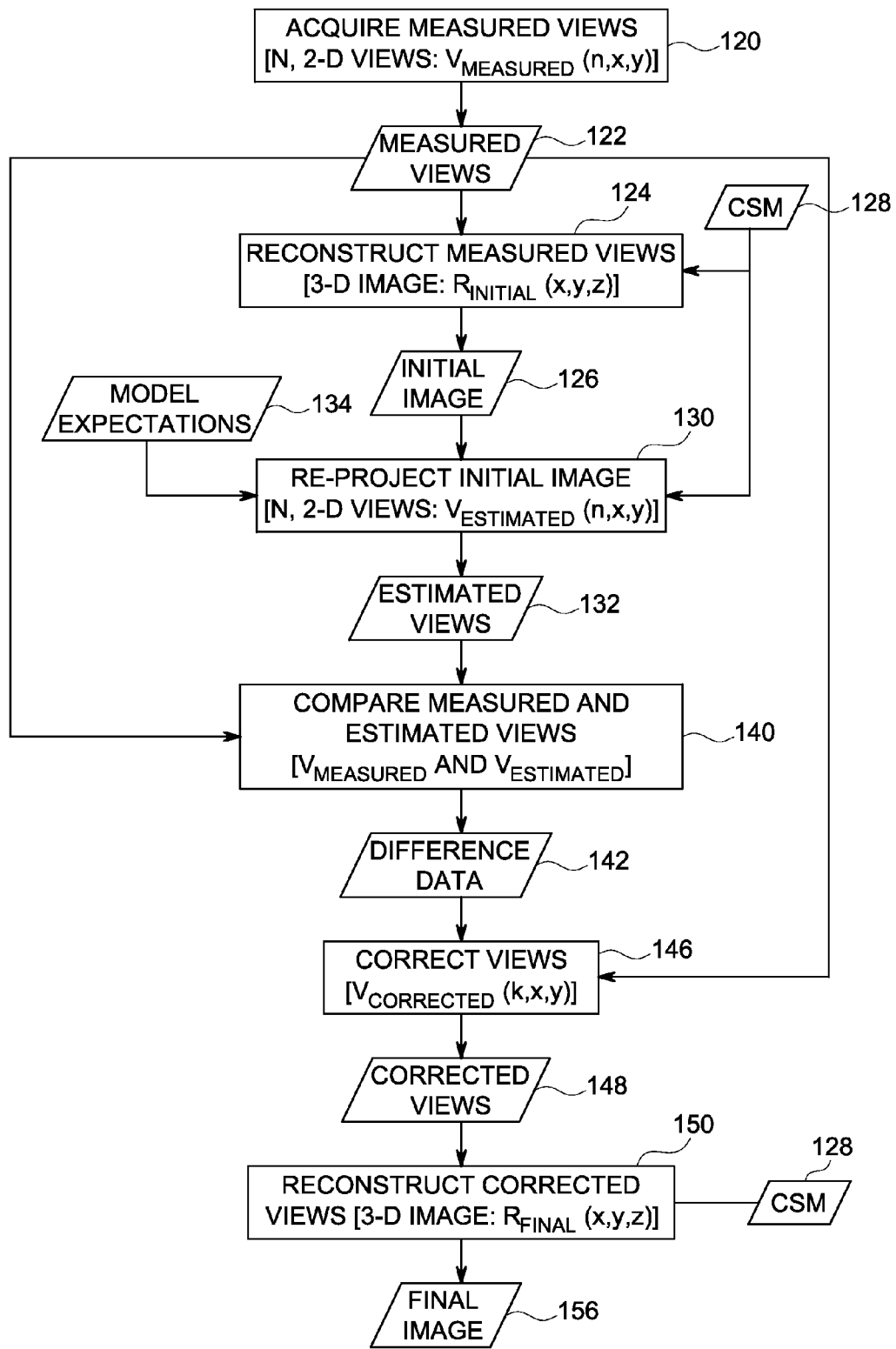
FIG. 12 depicts a first flow diagram of processor-executable logic for addressing image artifacts attributable to out-of-field sources, in accordance with aspects of the present disclosure.

With the foregoing in mind and turning to FIG. 12, one example of an algorithm that may be implemented as image processing control logic that is executable on a processor-based system is depicted. In this example, N measured views 122 ($V_{measured}$) are acquired (block 120) by a SPECT system at various positions about the organ or region of interest of a patient. Each measured view 122 is a two-dimensional image some or all of which encompass at least part of the organ or region of interest in the patient. In one example, some of the measured views 122 also include image data generated in response to radiation emitted by one or more out-of-field sources.

An initial reconstruction (block 124) is performed on the measured views 122 to generate an initial reconstructed image ($R_{initial}$) 126, e.g., a reconstructed volume encompassing the region or organ of interest. In an implementation where the measured views 122 are acquired using a conventional collimated camera, the initial reconstruction may be performed using a filtered back projection or an iterative reconstruction algorithm. In other implementations where the measured views 122 are acquired using multiple pinhole cameras, the initial reconstruction may be performed using an iterative reconstruction algorithm or other suitable reconstruction algorithm. In the initial reconstruction (block 124) a camera system matrix (CSM) 128 may be employed in the reconstruction that relates the response at the various detector elements to the voxels in the field of view. In certain embodiments, additional corrections or processing may be performed in conjunction with reconstructing the initial image 126. For example, attenuation correction and/or scatter correction may be performed as part of or subsequent to reconstructing the initial image 126. Optionally, reconstructing the initial image 126 involves only a subset of measured views 122. For example views from positions that are known to have higher probability of including contributions from out of field sources may be excluded.

The initial image 126 is typically dominated by the organ or region of interest, but may also contain artifacts or irregularities that may be attributed to the radiation contribution of one or more out-of-field sources. In one implementation, the region or organ of interest may be segmented in the initial image 126 based on identifying a contiguous area or areas of high voxel values (e.g., voxel values above a specified threshold value). In such an embodiment, an expansion step may also be performed to slightly expand the segmented region to include adjacent or other neighboring pixels to ensure that the region or organ of interest is encompassed by the segmented region. In some embodiments, an atlas of known body organs may be used for identification of the organs within the reconstructed initial image. Such atlases are known in the art and prepared for a variety of organs for various types of patients and conditions. The organs in the atlas may be matched (for example by image shift, rotation, scaling and/or other distortions) to the initial image. The initial image may then be replaced with the matched atlas organ. In this way, a defective organ in the initial image, which may be missing a physiologically non-functioning section, may be replaced with a matched full size organ.

If the organ or region of interest is identified and/or segmented in the initial image 126, various optional actions may be taken based on this segmentation. For example, in one embodiment, those voxels not identified as being in the segment corresponding to the region of interest voxels (e.g., the non-organ of interest voxels) may be effectively removed from the initial image 126 by setting the values of these voxels to zero. In another implementation, the values of the non-organ of interest voxels may be set to a value corresponding to an average background value, such as the average voxel value for those voxels not assigned to the organ or region of interest segment. In other embodiments, the values of the non-organ of interest voxels may be smoothed and/or a positivity of voxel value constraint may be enforced, if needed. In other embodiments, none of these actions may be performed.

In one implementation, the initial image 126 is re-projected (block 130) based on model or a priori expectations 134 to generate N estimated views ($V_{estimated}$) 132. Typically, the model 134 used in re-projection process 130 is based on the known parameters of the imaging system and may be based on its known construction or on results of experimental measurements (for example using known sources or phantoms) performed with the system. The model or other expectations 134 may correspond to a model or expectations typically employed in an iterative reconstruction algorithm to systematically test and address deviations and/or artifacts in reconstructed images. In such a re-projection the camera system matrix 128 may be employed in the re-projection to properly model the physical and geometric effects of the camera or detector assembly. Likewise, to the extent that attenuation and/or scatter correction were previously employed, the appropriate attenuation and/or scatter correction models may also be employed in the re-projection process.

The measured views 122 and the estimated views 132 may be compared (block 140) to identify views or regions in views that are likely to be affected by out-of-field sources. In one embodiment, the affected views or regions may be identified by identifying regions or pixels that are different (i.e., difference data 142) in the measured views 122 and estimate views 132. Statistical measures may be employed to determine the affected views or parts of the views. For example, pixels in which the difference between the measured and projected data is above a threshold are considered as affected. Threshold may be a preset fraction of the measured or projected values, or related to the noise (such as standard deviation of the values) estimated to for the view or the part of the view. In one implementation, the affected views or regions are treated (e.g., processed) differently than those regions or views that are not affected by out-of-field sources, thereby reducing or eliminating artifacts in the final image 156 that may be attributed to out-of-field radiation contributions. Further, an expansion of the identified affected regions may be performed in some embodiments such that pixels or regions adjacent to those areas deemed to be affected by out-of-field sources may also be differently treated, i.e., are deemed to also be part of the affected regions. That is neighboring or adjacent regions to those regions that are identified as affected may also be differentially processed to address out-of-field source effects.

In one implementation, the affected regions or views may be eliminated or downweighted (i.e., penalized) in the data set to reduce the effects of the out-of-field contributors of radiation. For example, in one embodiment a correction (block 146) may be performed and corrected views 148 generated by subtracting an estimated value or contribution of the out-of-field sources (e.g., difference data 142) from the corresponding measured views 122. The corrected views 148 may then be reconstructed (block 150) to generate a final image 156. In other embodiments, the affected regions or views may be differently processed than pixels not determined to be in an affected region or view, such as by modification or adjustment of the respective camera system matrix 128. Thus, the reconstruction of the final image may be based on the original camera system matrix 128, as depicted, or on an updated or revised camera system matrix. An example of such an updated system matrix would be one in which the projection data is reduced by some factor (e.g., f<1) for an affected pixel $P_i$ in the projection, and the system matrix factors describing the relationship between pixel $P_i$ and voxels (MO are replaced by $f^*M_{ij}$. The factor f would be smallest for the most affected pixels (i.e., the most affected pixels would be penalized or downweighted the most), and could taper to 1.0 as distance from the affected area increases and/or an unaffected area is entered.

In certain embodiments, the final image 156 may be provided (e.g., displayed) along with the initial reconstructed image 126, such as in a side-by-side display arrangement. Such an arrangement allows the reviewer to see and compare the image with and without additional processing. Similarly, in other implementations the reviewer may be allowed to view the measured views along with the identified affected regions, such as with the affected region superimposed on the views.

With the foregoing in mind, certain examples of embodiments and implementations are discussed in greater detail below to facilitate explanation of how out-of-field source effects may be identified and/or addressed. For example, in one implementation, the comparison 140 may take the form of a pixel-by-pixel subtraction of respective measured views 122 and corresponding estimated views 132 by which one or more difference views are generated:

$$DV(k,x,y) = MV(k,x,y) - EV(k,x,y) \qquad (1)$$

In such an approach, the difference views may be dominate by out-of-field source radiation. As a result, statistically high pixel values in a difference view may be an indication of an affected region. That is, pixels in a difference view having a value above (or below) a specified threshold may be identified as corresponding to an affected region of the corresponding measured view. Alternatively, affected regions smoothing and/or enforced positivity may be utilized to identify affected regions within the difference views.

In other embodiments, one or more thresholds may be employed to identify those pixels, regions, or views classified as affected regions. For example, in one embodiment, the average pixel value in a difference view may be calculated using all of the available pixel values or, alternatively, using only the positive pixel values. Similarly, a statistical standard deviation may be calculated for the relevant pixel sample. A suitable threshold for a difference view may then be calculated based on the average pixel value and on the associated standard deviation for that difference view, such as in accordance with:

$$T_{AR} = (a)(APV) + (b)(SD) \qquad (2)$$

where $T_{AR}$ is the threshold pixel defining whether a pixel is classified as being in an affected region or not, APV is the average pixel value for some or all of the pixels in a given different view, a is a weight factor applied to the APV, SD is the statistical standard deviation for the pixels used to calculate the APV, and b is the weight factor applied to the SD. For example, in one implementation, a may be set to 3 and b may be set to 0 such that:

$$T_{AR} = (3)(APV). \qquad (3)$$

In another implementation, a may be set to 1.5 and b may be set to 2 such that:

$$T_{AR} = (1.5)(APV) + (2)(SD). \qquad (4)$$

Pixels in the difference view having values greater than the determined threshold may be marked, tagged, or otherwise identified as being affected pixels.

In certain embodiments, pixels identified as affected pixels may be used to identify larger affected regions within each difference image. For example, any view having greater than a specified number or percentage of affected pixels may be defined as being an affected region or view. Likewise, any view having greater than a specified number or percentage of affected pixels with a cleaning mask (discussed below) generated for that view may be defined as being an affected region or view.

More generally, the affected pixels in each view may be provided to a segmentation process, which may employ logic that takes into account pixel intensities, adjacency or proximity to other affected pixels, contiguous regions, and so forth to define an affected region or segment in the respective view. In such implementations, the affected regions may be identified or determined so as to be full, to have smoothed edges, to be contiguous, to be a single affected region, and so forth.

An affected region, once defined or segmented, may be expanded (i.e., undergo an expansion process) to ensure that all affected pixels are encompassed by the affected region. In certain implementations, an expanded affected region may partially overlap the projection of the organ or region of interest. Such an overlap may be desirable as, within the region encompassed by the projection of the organ of interest the counts may be so high that a statistical threshold may not be sensitive enough to distinguish affected pixels. That is, there may be out-of-field source effects that are masked or hidden by the image data associated with the organ of interest.

Figure 13:
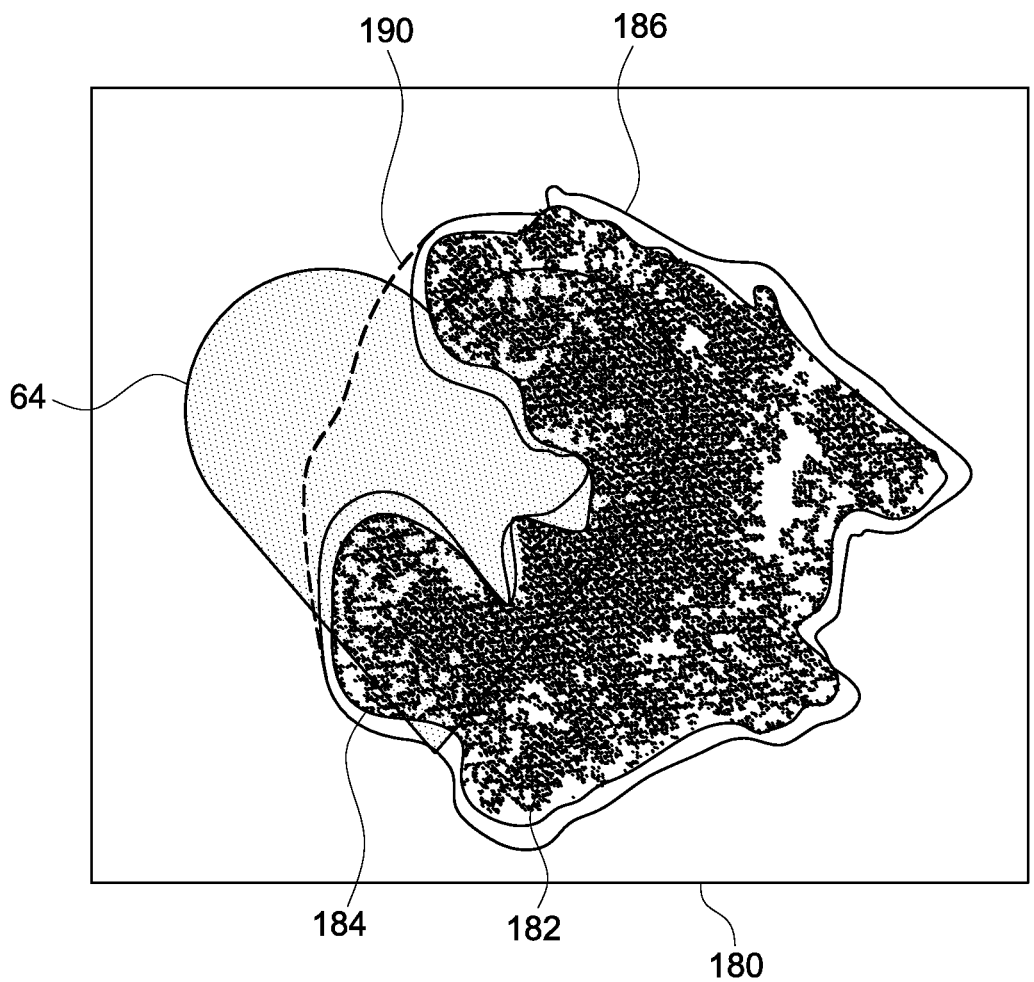
FIG. 13 depicts an example of a view depicting suitable expansion of an affected region identified in the view, in accordance with aspects of the present disclosure.

By way of example of the preceding concepts, and turning to FIG. 13, a view 180 is depicted in which both an organ of interest (here heart 64) and an out-of-field source of radiation is depicted. The out-of-field source of radiation may initially be distinguished by identifying a number of affected pixels 182 generally spread about the region affected by the out-of-field source, i.e., affected region. Due to thresholding effects, noise, and general measurement variability, the affected pixels may not describe a continuous or smooth area, particularly where the affected region and the organ of interest overlap. The affected pixels 182, therefore, may be used as the basis for a segmentation process by which a segmented affected region 184 is initially determined. The segmented affected region 184 may be contiguous and may be smoothed at the edges based on assumptions made as part of the segmentation process. In addition, in the depicted example, the segmented affected region 184 may undergo an expansion to generate a first expanded affected region 186 which encompasses neighboring or adjacent pixels to the segmented affected region 184. In this manner, it may be more likely that all of the affected pixels are encompassed in the first expanded affected region 186.

In the depicted example, a second expansion may also be performed in an area of overlap between the affected region and the organ of interest to generate a second expanded affected region 190. In particular, due to the overlap between the organ of interest and the affected region, there may be greater uncertainty as to the presence of out-of-field source effects in the vicinity of the organ of interest due to the strong signal associated with the organ of interest. The second expansion takes into account the overlap between the affected region and the organ of interest to increase the certainty that all affected pixels are encompassed by the region deemed to be affected by the out-of-field source. For example expansion 190 may be based on requiring that the affected region is convex, or has limited curvature or is matched to a projection of an organ from a known atlas. The effects of the affected region may then be addressed as discussed herein, even in areas of overlap with the organ or region of interest.

In certain embodiments, a cleaning operation may be performed that incorporates one or more masks derived based upon the organ or region of interest, such as after segmentation of the organ or region of interest in the initial image 126, as discussed above. For example, in one such embodiment the organ or region of interest may be clearly observed in the expected views 132 as having statistically higher pixel values. The projection of the organ or region of interest on each view may be used as a mask and pixels outside the mask region in each view may be set to zero or a background level. In certain implementations, the pixels or region associated with the organ or region of interest may undergo an expansion prior to determining the mask region in each view to ensure that no relevant pixels are inadvertently masked out.

Optionally, a synthetic object may be generated by constructing a volumetric image having all voxel values set to zero except those in a volume presumably occupied by the organ or region of interest. As will be appreciated, this volume may be expanded to include adjacent or other proximate voxels so as to ensure it includes the organ or region of interest. The synthetic object may be re-projected to create masks for each of the desired views. Masks generated in this manner may then be utilized as discussed above to clean the respective views. As will be appreciated, though a cleaning operation (such as a cleaning operation utilizing a mask) may be performed in certain embodiments, in other embodiments, no such cleaning operation may be performed.

With respect to the correction of pixel values in affected regions and/or the differential processing of such pixels, a variety of approaches may be employed. In one implementation the pixel values within an affected region may be replaced with other values, such as values derived using the estimated views 132 or a suitable model. In certain such embodiments, an entire view containing an affected region may be replaced by the corresponding estimated view 132. In other embodiments, the pixel values in an affected region may be replaced with a weighted average of the corresponding measured view 122 and estimated view 132 such as where the affected pixel value is set according to:

$$\text{Affected Pixel Value} = (a)(MV) + (1-a)(EV) \qquad (5)$$

where 0<a<1, a is a suitable weight, MV is the corresponding pixel value in the corresponding measured view, and EV is the corresponding pixel value in the corresponding estimated view. In other embodiments, pixel values of an affected region within a difference view may undergo a smoothing operation, after which these pixel values may be subtracted from the corresponding pixel values of the corresponding measured view. Similarly, in another implementation an entire difference view may undergo a smoothing operation and may be subtracted from a corresponding measured view containing an affected region.

In addition, in one implementation affected pixels and the corresponding system matrix values may be replaced or altered with a suppressed factor (e.g., a downweighted or penalized value). For example, the pixel value may be decreased by a factor corresponding to the ratio of "presumed in-field" and "presumed out of field" counts. The system matrix elements may then be scaled by the same ratio to maintain the correct weighting. Such an approach would reduce the effect of these views without completely throwing them away, and without replacing actual data with an estimate.

In an embodiment where the measured views are corrected, such as to set the pixel values in the affected regions to a background value to generate corrected views 148, the final reconstruction 150 may be a standard reconstruction approach, such as based on filtered back projection or a suitable iterative reconstruction algorithm.

Figure 14:
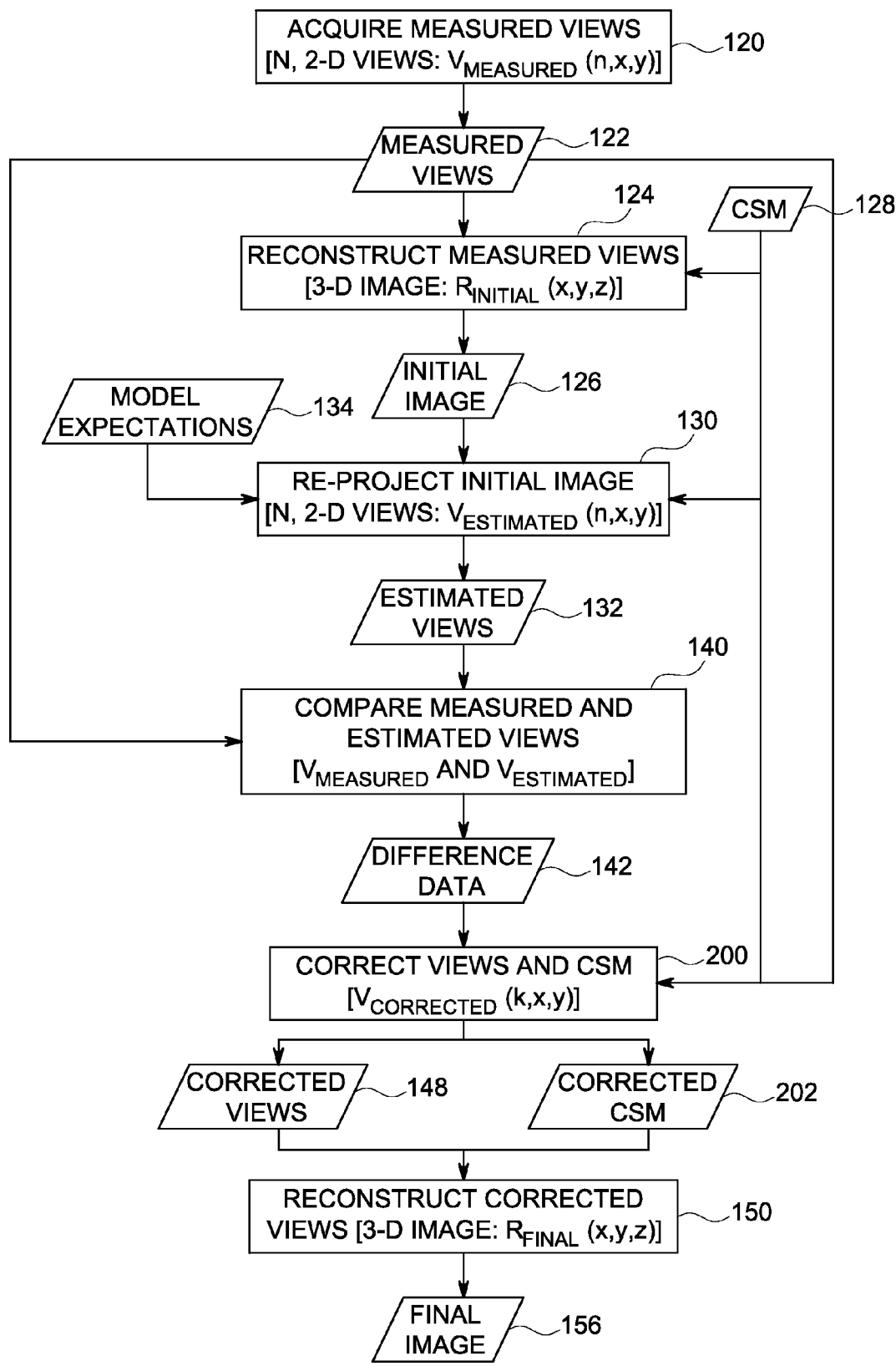
FIG. 14 depicts a second flow diagram of processor-executable logic for addressing image artifacts attributable to out-of-field sources, in accordance with aspects of the present disclosure.

In other embodiments, such as that depicted in FIG. 14, differential processing of the identified affected regions may be performed. For example, in one embodiment the identified affected regions may be differentially treated by adjusting (e.g., reducing) (block 200) values in the camera system matrix 128 to generate a corrected camera system matrix 202 that is used in the final reconstruction 150. By way of example, a camera system matrix value corresponding to an affected pixel may be replaced such that:

$$\text{Corrected CSM value} = (a)(\text{Original CSM value}) \quad (6)$$

where 0<a<1. As will be appreciated, a may be chosen to correspond to a factor by which a related pixel value associated with that element of the system matrix is adjusted. That is, a may correspond to a scale factor or weight by which a corresponding pixel or pixels are penalized due to identified contribution from out-of-field sources. In this manner, the relationship in the system matrix between detector response and observed voxel intensity can be maintained while still accounting for out-of-field radiation contributions.

Technical effects of the invention include generation of a reconstructed volume in which the effects of out-of-field source emissions are reduced or eliminated. Technical effects may include comparing measured and estimated views to generate information about differences between the views that is indicative of out-of-field radiation emissions that may result in artifacts. An artifact-free or artifact-reduced final image may be generated by based upon this identification of the differences between the measured and estimated views. In some embodiments, corrected views may be generated based upon the identified differences. In other embodiments, differential processing may be performed on affected view regions identified based on the differences and on other view regions.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An image analysis system, comprising:
one or more processing components configured to receive measured views that generally encompass an organ or region of interest from which radiation is emitted by decay of a radiopharmaceutical, wherein some, but not all, of the measured views include radiation contributions from a secondary organ or tissue that is not of interest, and to execute one or more executable routines stored in a memory;
the memory storing the one or more executable routines, wherein the stored routines, when executed, reconstruct the measured views to generate an initial image using an initial camera system matrix that models the physical and geometric relationship of a detector used to acquire the measured views, generate a corresponding estimated view for each measured view using the initial image, compare each measured view with the corresponding estimated view to derive an indication, if any, of the radiation contributions from the secondary organ or tissue present in each measured view, and use the indications to update the camera system matrix to form an updated camera system matrix that is used to reconstruct a final image in which the radiation contributions from the secondary organ or tissue are reduced or eliminated; and
interface circuitry configured to allow user interaction with the image analysis system.

2. The image analysis system of claim 1, wherein the detector comprises:
one or more detector assemblies suitable for detecting radiation emitted from a patient;
data acquisition circuitry configured to acquire signals from the one or more detector assemblies, wherein the measured image views are or are derived from the acquired signals.

3. The image analysis system of claim 2, wherein the one or more detector assemblies comprise pin-hole gamma cameras or collimated detector assemblies suitable for measuring gamma rays.

4. The image analysis system of claim 2, comprising a positioner capable of moving the one or more detector assemblies with respect to the patient.

5. The image analysis system of claim 1, wherein the derived indication comprises one or more of an identification of pixels, regions, or views affected by the radiation contributions from the secondary organ or tissue.

6. The image analysis system of claim 1, wherein reconstructing the final image comprises effectively subtracting image contributions from the secondary organ or tissue from those image areas with no such indication.

7. The image analysis system of claim 1, wherein updating the camera system matrix comprises applying scaling factors to reduce the contributions of affected pixels to respective voxels to which the affected pixels contribute.

8. The image analysis system of claim 7, wherein the scaling factors are derived from a ratio of radiation counts determined to be from within the field of view to radiation counts determined to be from outside the field of view.

9. The image analysis system of claim 1, wherein reconstructing the final image comprises downweighting or otherwise penalizing those areas where there is an indication of radiation contributions from the secondary organ or tissue.

10. One or more non-transitory machine readable media encoding routines that, when executed by a processor, cause acts to be performed comprising:

accessing a plurality of different measured views, wherein the measured views depict a radiation contribution from an organ or region of interest and wherein some but not all of the measured views also include a secondary radiation contribution from a secondary organ or tissue that is not of interest;

reconstructing the plurality of measured views to generate an initial image using an initial camera system matrix that relates detector response to observed voxel intensity;

re-projecting the initial image using an updated camera system matrix updated to include one or more scaling factors to generate a plurality of cleaned views in which those pixels outside the area are set to an adjusted value; and reconstructing a final image based at least in part upon the plurality of cleaned views.

11. The one or more machine readable media of claim 10, wherein the adjusted value comprises zero, a background value, or an average value.

12. The one or more machine readable media of claim 10, wherein the updated camera system matrix applies the scaling factors to reduce the contributions of affected pixels to respective voxels to which the affected pixels contribute.

13. The one or more machine readable media of claim 12, wherein the scaling factors are derived from a ratio of radiation counts determined to be from within the field of view to radiation counts determined to be from outside the field of view.

14. An image reconstruction method, comprising the acts of:

acquiring a plurality of measured views generally representing the radiation emitted by an organ or region of interest as seen from different positions, wherein some but not all of the measured views includes radiation emitted by an out-of-field source with respect to the fields-of-view of at least some of the remaining measured views;

generating a corresponding estimated view for at least some of the measured view;

comparing at least one measured view with the corresponding estimated view to identify one or more affected regions in the one or more measured views that include radiation emitted by the out-of-field source; and generating a final image where the contributions of the identified affected regions are reduced or eliminated by differentially processing the one or more affected regions and those regions that are not affected by radiation emitted by the out-of-field source by performing an image subtraction to remove the contributions of the out-of-field source from the one or more affected regions.

15. The image reconstruction method of claim 14, wherein comparing a measured view with the corresponding estimated view to identify the one or more affected regions comprises performing a pixel-by-pixel subtraction of said measured view from said corresponding estimated view to generate respective difference views.

16. The image reconstruction method of claim 14, wherein the one or more affected regions comprise one or more of affected pixels, affected areas derived based upon identified affected pixels, or affected views determined to include affected pixels above a desired limit.

17. The image reconstruction method of claim 14, comprising expanding the one or more affected regions to include adjacent pixels or regions.

18. The image reconstruction method of claim 14, generating the final image where the contributions of the identified affected regions are reduced or eliminated comprises eliminating, downweighting, or otherwise penalizing pixels of the affected regions in the reconstruction of the final image.

19. The image reconstruction method of claim 14, wherein the one or more affected regions are identified based upon a threshold.

* * * * *